US010287326B2

(12) United States Patent
Jan et al.

(10) Patent No.: US 10,287,326 B2
(45) Date of Patent: May 14, 2019

(54) ANTI-INFLAMMATORY PROPERTIES OF A SURFACE PROTEIN OF PROPIONIBACTERIUM FREUDENREICHII

(71) Applicants: INSTITUT NATIONAL DE LA RECHERCHE AGRONOMIQUE (INRA), Paris (FR); INSTITUT PASTEUR DE LILLE (IPL), Lille (FR)

(72) Inventors: Gwenael Jan, Rennes (FR); Benoit Foligne, Lille (FR); Helene Falentin, Mordelles (FR); Stephanie-Marie Deutsch, Pace (FR)

(73) Assignees: INSTITUT NATIONAL DE LA RECHERCHE AGRONOMIQUE (INRA), Paris (FR); INSTITUT PASTEUR DE LILLE (IPL), Lille (FR)

( * ) Notice: Subject to any disclaimer, the term of this patent is extended or adjusted under 35 U.S.C. 154(b) by 0 days.

(21) Appl. No.: 15/326,759

(22) PCT Filed: Jul. 7, 2015

(86) PCT No.: PCT/EP2015/001379
§ 371 (c)(1),
(2) Date: Jan. 17, 2017

(87) PCT Pub. No.: WO2016/008571
PCT Pub. Date: Jan. 21, 2016

(65) Prior Publication Data
US 2017/0204145 A1 Jul. 20, 2017

(30) Foreign Application Priority Data
Jul. 15, 2014 (EP) .................................. 14002429

(51) Int. Cl.
A61K 38/00 (2006.01)
C07K 14/195 (2006.01)
A61K 38/16 (2006.01)
C12Q 1/04 (2006.01)

(52) U.S. Cl.
CPC .......... C07K 14/195 (2013.01); A61K 38/164 (2013.01); C12Q 1/04 (2013.01); A61K 38/00 (2013.01); G01N 2333/195 (2013.01); G01N 2550/00 (2013.01)

(58) Field of Classification Search
None
See application file for complete search history.

(56) References Cited

U.S. PATENT DOCUMENTS

| 4,861,719 A | 8/1989 | Miller |
| 5,278,056 A | 1/1994 | Bank et al. |
| 5,882,877 A | 3/1999 | Gregory et al. |
| 6,013,516 A | 1/2000 | Verma et al. |
| 6,127,175 A | 10/2000 | Vigne et al. |
| 6,464,998 B1 | 10/2002 | Beuzard et al. |
| 8,241,684 B2 | 8/2012 | Uchida et al. |
| 9,476,056 B2 * | 10/2016 | Jan .................. C07K 14/70578 |
| 2013/0108584 A1 * | 5/2013 | Jan .................. C07K 14/70575 424/93.2 |
| 2014/0154213 A1 * | 6/2014 | Jan .................. C07K 14/70578 424/93.2 |
| 2017/0204145 A1 * | 7/2017 | Jan ....................... C07K 14/195 |
| 2018/0015130 A1 * | 1/2018 | Berry .................. A61K 35/741 |

FOREIGN PATENT DOCUMENTS

| EP | 1 738 761 A1 | 1/2007 | |
| EP | 2974735 A1 * | 1/2016 | ........... A61K 38/164 |
| EP | 3024469 A1 * | 6/2016 | ............ A61K 35/74 |
| EP | 3169346 A1 * | 5/2017 | |
| WO | 94/19478 A1 | 9/1994 | |
| WO | 95/14785 A1 | 6/1995 | |
| WO | 96/22378 A1 | 7/1996 | |
| WO | WO-2015011250 A1 * | 1/2015 | ............ A61K 35/74 |
| WO | WO-2016008571 A1 * | 1/2016 | ........... A61K 38/164 |
| WO | WO-2017050773 A1 * | 3/2017 | ............ A61K 35/74 |

OTHER PUBLICATIONS

Foligne et al, Gut, Aug. 2013, 62:1227-1228, published online first: Feb. 6, 2013 (Year: 2013).*
Deutsch et al, Scientific Reports, 2017, 7; 46409, abstract only (Year: 2017).*
Deutsch et al, Applied and Environmental Microbiology, Mar. 2012. 78/6:1765-1775, published ahead of print: Jan. 13, 2012 (Year: 2012).*
Falentin et al, Standards in Genomic Sciences, 2016, 11:6, 6 pages (Year: 2016).*
LeMarechal et al, Data in Brief, 2014, 1:46-50, available online: Sep. 22, 2014 (Year: 2014).*
LeMarechal et al, Journal of Proteomics, 112 (2015) 447-461, available online: Aug. 20, 2014 (Year: 2014).*
Ple et al, Mol. Nutr. Food Res., 2016, 60:935-948 (Year: 2016).*
Thierry et al, International Journal of Food Microbiology, 149 (2011) 19-27, available online: May 8, 2011 (Year: 2011).*
Foligne et al, Applied and Environmental Microbiology, Dec. 2010. 76/24:8259-8264. published ahead of print on Oct. 22, 2010 (Year: 2010).*

(Continued)

Primary Examiner — Nita N. Minnifield
(74) Attorney, Agent, or Firm — Young & Thompson

(57) ABSTRACT

Disclosed is a polypeptide including or consisting of the amino acid sequence SEQ id n°:1, for use in the treatment or prevention of an inflammatory disease. It further encompasses a nucleic acid sequence encoding a polypeptide, a vector including a nucleic acid and a host cell including a nucleic acid sequence and/or a vector, for use in the treatment or prevention of an inflammatory disease. Also disclosed is a pharmaceutical composition or a food composition including a polypeptide, a nucleic acid sequence, a vector or a host cell and a pharmaceutically acceptable carrier or a dairy product, for the treatment of inflammatory disease. Additionally, a method for the screening of bacteria having immunomodulatory properties is disclosed.

8 Claims, 11 Drawing Sheets
Specification includes a Sequence Listing.

(56) References Cited

OTHER PUBLICATIONS

Okada et al, Gut, 2006, 55:681-688, published online first: Nov. 18, 2005 (Year: 2005).*
Greenspan et al Nature Biotechnology, Oct. 1999, 17:936-937 (Year: 1999).*
Bixler et al, Synthetic Vaccines, vol. I, 1987, pp. 39-71 (Year: 1987).*
Blythe et akl, Protein Science, 2005, 14:246-248, originally published online Dec. 2, 2004 (Year: 2004).*
Bowie et al, Science, New Series, vol. 247, No. 4948 (Mar. 16, 1990, pp. 1306-1310 (Year: 1990).*
Burgess et al, JBC, Nov. 1990, 111:2129-2138 (Year: 1990).*
Kumar et al, PNAS, USA, Feb. 1990, 87/4:1337-1341 (Year: 1990).*
Lazar et al, Molecular and Cellular Biology, Mar. 1988, 82:1247-1252 (Year: 1988).*
Deutsch et al, Scientific Reports, 2017, 7:46409. 14 pages. published: Apr. 13, 2017 (Year: 2017).*
Carmo Fillipe et al, Frontiers in microbiology, (2018) vol. 9, pp. 1807. abstract only. Electronic Publication Date: Aug. 17, 2018 (Year: 2018).*
Rabah et al, Food Research International. 2018. 106:712-721. available online: Jan. 31, 2018 (Year: 2018).*
Anne Thierry et al: "New insights into physiology and metabolism of Propionibacterium freudenreichir", International Journal of Food Microbiology, vol. 149, No. 1, May 8, 2011 (May 8, 2011), pp. 19-27, XP028249371, ISSN: 0168-1605, [retrieved on May 8, 2011], DOI: 10.1016/J.IJFOODMICRO.2011.04.026.
Helene Falentin et al: "The Complete Genome of Propionibacterium freudenreichii CIRM-BIA1T, a Hardy Actinobacterium with Food and Probiotic Applications", PLOS ONE, vol. 5, No. 7, Jan. 1, 2010 (Jan. 1, 2010), pp. e11748, XP055013560, ISSN: 1932-6203, DOI: 10.1371/journal.pone.0011748.
International Search Report, dated Oct. 7, 2015, from corresponding PCT application.

* cited by examiner

MSVRKSLTGMALGLALTITPLAGAVPASADTAPAPKDAITKAADWLVNDYNTNCLGDKQTSYSCSNGGLADVILALSSTGDAKYADE
ISTMMTNLAPQVASYTKDNAGATAKIITVIAAHQKPSAFGGNDLVGQLQALNAENPAGGGAWGPQLSMVALT
RAGETVPEALIDATVDKQNSKGGFGWGGDTGDGDNTAIGMMATAAVAKGNPRAADSLAKAVAWAQDPANLTTDDTGSYWT
NYSPTNTAGMMLMAIGDVNDPKIDVSKQMDFLIGRQLPSGAFSNTLKGTNDNAMATIQALQGLTMHGYLTASAGQKNDPG
TGGGTTDPGTGGGTGGGSTGGGSTGGGGSTGGGGVVTPPVTQAFTDVAPSNMYFTEIQWAAANNVITG
WKNADGIASFRPLDITHRDAMAAFLYRLSGSPSYTAPATSPFTDVNPSNQFYKEICWLASQNIITGWPDGSFRPLDNVNR
DAMAAFLYRYSQVSGFQAPAASPFADVTPGSQFYTEMSWLSANGISTGWPDQTFRPVTPIARDAMITFIYRMKHAS

Figure 2

ANTI-INFLAMMATORY PROPERTIES OF A SURFACE PROTEIN OF PROPIONIBACTERIUM FREUDENREICHII

The present application claims the priority of the European patent application 14002429 filed on Jul. 15, 2014, which is herein incorporated by reference.

FIELD OF THE INVENTION

The present invention relates to the treatment of inflammatory diseases based on the discovery of a new anti-inflammatory protein.

BACKGROUND OF THE INVENTION

Inflammation is a natural biological process, which constitutes a normal part of the response to injuries or infections. This process contributes to the protection of the organism against intern or extern aggressions. However, a dysfunction of the inflammation mechanisms, particularly a persistent or too abundant inflammation may cause important painful and life threatening diseases. Such diseases comprise skin disorders, bowel disorders, some neurological disorders, arthritis, autoimmune diseases . . . . Among them, inflammatory bowel disease (IBD) is a group of disorders characterized by a chronic and relapsing inflammation of the gastrointestinal tract. The most common form of this group is the Crohn's disease. The pathogenesis involves an inappropriate and ongoing activation of the mucosal immune system driven by the presence of the intestinal microbiota in a genetically predisposed patient.

Now, several of these inflammatory diseases remain without treatment or without sufficient treatment. Thus, studying and finding new anti-inflammatory treatment strategies constitutes a major matter in medicine and biomedical research.

*Propionibacterium freudenreichii* is a beneficial bacterium used in the food industry as a vitamin producer, as a bio-preservative, as a cheese ripening starter and as a probiotic. It is known to adhere to intestinal epithelial cells and mucus, and to modulate important functions of the gut mucosa, including cell proliferation and immune response.

From U.S. Pat. No. 8,241,684, it was considered that *Propionibacterium freudenreichii* produces bifidogenic growth stimulators (BGSs) among which the active component thereof was 1,4-dihydroxy-2-naphthoic acid (DHNA); said DHNA being known to have effects on promoting the growth of bifidobacteria and improving inflammatory conditions of the mucosa in IBDs as well as suppressing infiltration of activated immune cells.

SUMMARY OF THE INVENTION

The present invention is based on the discovery by the present inventors of the anti-inflammatory properties of a distinct and specific component of the bacterium *Propionibacterium freudenreichii*.

The present invention relates to a polypeptide comprising or consisting of the amino acid sequence SEQ ID NO:1, for use in the treatment or prevention of an inflammatory disease.

Particularly, said inflammatory disease is a bowel inflammatory disease.

The invention further encompasses a nucleic acid sequence encoding a polypeptide of the invention, a vector comprising a nucleic acid of the invention and a host cell comprising a nucleic acid sequence and/or a vector of the invention, for use in the treatment or prevention of an inflammatory disease.

The invention also concerns a pharmaceutical composition comprising such a polypeptide, nucleic acid sequence, vector or host cell of the invention and a pharmaceutically acceptable carrier, preferably for the treatment or prevention of inflammatory disease.

The invention also relates to a method for the screening of bacteria having immunomodulatory properties comprising the step of:
a) Culturing a bacterium in a medium comprising sodium lactate and casein hydrolysate,
b) Preparing a protein sample extract from the bacterium of step a),
c) Measuring the expression level of the polypeptide comprising or consisting of the amino acid sequence SEQ id n°:1, a conservative derivative or a fragment thereof, in the protein sample extract as prepared in step b), and
d) Selecting the bacteria expressing said polypeptide as defined in step c).

Finally, the invention provides a method for preventing or treating an inflammatory disease in a patient in need thereof, said method comprising the step of administrating said patient with a therapeutically effective amount of a polypeptide, a nucleic acid sequence a vector or a host cell of the invention.

BRIEF DESCRIPTION OF THE DRAWINGS

FIG. 2 shows the amino acid sequence of slpB protein.

DETAILED DESCRIPTION OF THE INVENTION

Polypeptides of the Invention

Figure 1:
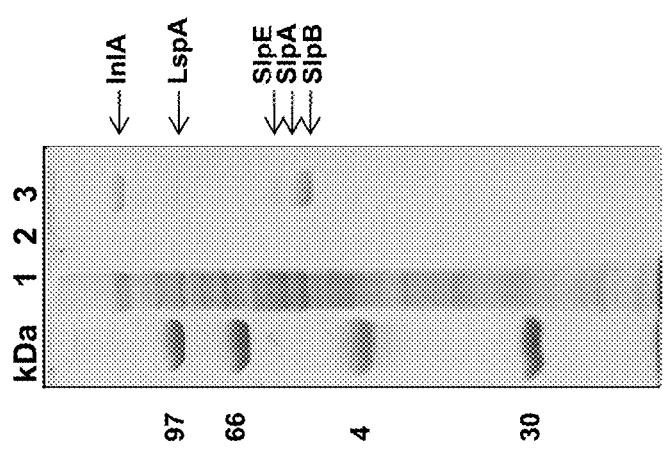
FIG. 1 shows a SDS PAGE gel of Guanidine hydrochloride extract of *P. freudenreichii*.

A first aspect of the invention relates to a polypeptide comprising or consisting of the amino acid sequence SEQ ID NO:1, for use in the treatment or prevention of an inflammatory disease.

```
                                        SEQ id no: 1
MSVRKSLTGMALGLALTITPLAGAVPASADTAPAPKDAITKAADWLVNDY

NTNCLGDKQTSYSCSNGGLADVILALSSTGDAKYADEISTMMTNLAPQVA

SYTKDNAGATAKIIITVIAAHQKPSAFGGNDLVGQLQALNAENPAGGGAW

GPQLSMVALTRAGETVPEALIDATVDKQNSKGGFGWGGDTGDGDNTAIGM

MATAAVAKGNPRAADSLAKAVAWAQDPANLTTDDTGSYWTNYSPTNTAGM

MLMAIGDVNDPKIDVSKQMDFLIGRQLPSGAFSNTLKGTNDNAMATIQAL

QGLTMHGYLTASAGQKNDPGTGGGTTDPGTGGGTGGGSTGGGSTGGGGST

GGGGSTGGGGSTGGGGVVTPPVTQAFTDVAPSNMYFTEIQWAAANNVTTG

WKNADGTASFRPLDTTHRDAMAAFLYRLSGSPSYTAPATSPFTDVNPSNQ

FYKEICWLASQNITTGWPDGSFRPLDNVNRDAMAAFLYRYSQVSGFQAPA

ASPFADVTPGSQFYTEMSWLSANGISTGWPDQTFRPVTPIARDAMITFIY

RMKHAS
```

The term "inflammatory disease" has its general meaning in the art and refers to any disease and condition associated with inflammation. The term may include, but is not limited to, (1) inflammatory or allergic diseases such as systemic anaphylaxis or hypersensitivity responses, drug allergies, insect sting allergies; inflammatory bowel diseases, such as Crohn's disease, ulcerative colitis, pouchitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; respiratory allergic diseases such as asthma, allergic rhinitis, hypersensitivity lung diseases, and the like, (2) autoimmune diseases, such as arthritis (rheumatoid and psoriatic), osteoarthritis, multiple sclerosis, systemic lupus erythematosus, diabetes mellitus, glomerulonephritis, and the like, (3) graft rejection (including allograft rejection and graft-v-host disease), and (4) other diseases in which undesired inflammatory responses are to be inhibited (e. g., atherosclerosis, myositis, inflammatory CNS disorders such as stroke and closed-head injuries, neurodegenerative diseases, Alzheimer's disease, encephalitis, meningitis, osteoporosis, gout, hepatitis, nephritis, sepsis, sarcoidosis, conjunctivitis, otitis, chronic obstructive pulmonary disease, sinusitis and Bechet's syndrome).

In a particular embodiment of the invention, said inflammatory disease is an inflammatory bowel disease, comprising Crohn's disease, ulcerative colitis, ileitis, pouchitis and enteritis.

In the context of the invention, the term "treating" or "treatment" means reversing, alleviating, inhibiting the progress of, or preventing the disorder or condition to which such term applies, or one or more symptoms of such disorder or condition. The term "preventing" or "prevention" refers to preventing the disease or condition from occurring in a subject which has not yet been diagnosed as having it.

As used herein, the polypeptide of the invention encompasses derivatives or fragments thereof.

According to the invention, the term "derivative thereof" has its general meaning in the art and corresponds to an amino acid sequence or a nucleic acid sequence having at least 90% sequence identity to the referred amino acid sequence or nucleic acid sequence respectively, particularly 95%, and preferably 99%. The term "percentage of identity" between two amino acid sequences" or "percentage of identity between two nucleic sequences" refers to the percentage of identic nucleotides or amino acids between two compared sequences, said percentage being obtained with the best alignment of the whole sequence. The term "best alignment" means the alignment that permits to obtain the most elevated identity percentage. It can be realized by using various algorithms and methods well known in the art and computer programs based on said algorithms (GAP, BESTFIT, BLAST P, BLAST N, FASTA, TFASTA, Genetics Computer Group, 575 Science Dr., Madison, Wis., USA). Preferably, the BLAST algorithm is used.

According to the invention, the term "fragment" refers to a polypeptide being a part of an amino acid sequence of interest and having a length of at least 10 amino acids, particularly at least 15 amino acids, more particularly at least 20 amino acids, preferably at least 30 amino acids, more preferably at least 40 amino acids.

Preferably, said fragment has a length of less than 450 amino acids, particularly less than 400 amino acids, preferably less than 350 amino acids. The term is transposable to fragments of nucleic acid sequences.

As an example, said fragment may correspond to the amino acid 32 to 364 of SEQ id n°1 corresponding to the N-terminal extremity of maturated slpB protein or to fragments thereof.

According to the invention, said derivative and/or fragment of a polypeptide of the invention are conservative derivative or conservative fragments thereof.

By "conservative fragments" and "conservative derivatives" of a polypeptide of the invention, it is respectively meant fragments and derivatives which retain the function, namely the anti-inflammatory properties, of said polypeptide of the invention.

More specifically, a fragment or a derivative induces the secretion of IL-6 or IL-10 by PBMC. Such conservative fragments and conservative derivatives are functional equivalents of said polypeptide. They are "conservative" because they retain the biological function of the original polypeptide, more particularly because they retain an equivalent anti-inflammatory effect.

In a preferred embodiment, a polypeptide of the invention or a derivative or a fragment thereof is isolated.

As used herein, the term polypeptide encompasses polypeptides or proteins following post-translational modifications such as glycosylation, phosphorylation or other modifications of some amino acid residues.

The present invention thus relates to a polypeptide as described for use as an anti-inflammatory drug.

As used herein, the term "anti-inflammatory drug" refers to a drug that directly or indirectly reduces inflammation in a tissue.

A polypeptide of the invention may be produced by conventional automated peptide synthesis methods or by recombinant expression. General principles for designing and making peptides and proteins are well known to those of skill in the art.

A polypeptide of the invention may be synthesized in solution or on a solid support in accordance with conventional techniques. Various automatic synthesizers are commercially available and can be used in accordance with known protocols. A polypeptide of the invention may also be synthesized by solid-phase technology employing an exemplary peptide synthesizer such as a MODEL 433A from APPLIED BIOSYSTEMS INC. The purity of any given protein; generated through automated peptide synthesis or through recombinant methods may be determined using reverse phase HPLC analysis. Chemical authenticity of each peptide may be established by any method well known to those of skill in the art.

As an alternative to automated peptide synthesis, recombinant DNA technology may be employed wherein a nucleotide sequence which encodes a protein of choice is inserted into an expression vector, transformed or transfected into an appropriate host cell and cultivated under conditions suitable for expression as described herein below. Recombinant methods are especially preferred for producing longer polypeptides.

A variety of expression vector/host systems may be utilized to contain and express the peptide or protein coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV, tobacco mosaic virus, TMV) or transformed with bacterial expression vectors (e.g., Ti or pBR322 plasmid); or animal cell systems, including mammalian cell systems. Those of skill in the art are aware of various techniques for optimizing mammalian expression of proteins. Mammalian cells that are useful in recombinant protein productions include, but are not limited to, VERO cells, HeLa cells, Chinese hamster ovary (CHO) cell lines, COS cells (such as COS-7), W138, BHK, HepG2, Caco-2, HT29, HEK, HCT I16, 3T3, RIN, MDCK, A549, PC12, K562 and 293 cells.

Exemplary protocols for the recombinant expression of the peptide substrates or fusion polypeptides in bacteria, yeast and other invertebrates are known to those of skill in the art and a briefly described herein below.

In the recombinant production of the polypeptide of the invention, it would be necessary to employ vectors comprising a nucleic acid sequence encoding such a polypeptide. Methods of preparing such vectors as well as producing host cells transformed with such vectors are well known to those skilled in the art. The polynucleotide molecules used in such an endeavor may be joined to a vector, which generally includes a selectable marker and an origin of replication, for propagation in a host. These elements of the expression constructs are well known to those of skill in the art. Generally, the expression vectors include DNA encoding the given protein being operably linked to suitable transcriptional or translational regulatory sequences, such as those derived from a mammalian, microbial, viral, or insect genes. Examples of regulatory sequences include transcriptional promoters, operators, or enhancers, mRNA ribosomal binding sites, and appropriate sequences which control transcription and translation.

The choice of a suitable expression vector for expression of the polypeptide of the invention will of course depend upon the specific host cell to be used, and is within the skill of the ordinary artisan.

Expression requires that appropriate signals be provided in the vectors, such as enhancers/promoters from both viral and mammalian sources that may be used to drive expression of the nucleic acids of interest in host cells. Usually, the nucleic acid being expressed is under transcriptional control of a promoter. A "promoter" refers to a DNA sequence recognized by the synthetic machinery of the cell, or introduced synthetic machinery, required to initiate the specific transcription of a gene. Nucleotide sequences are operably linked when the regulatory sequence functionally relates to the nucleic acid sequence encoding the polypeptide of interest (i.e., a polypeptide of the invention, a derivative or fragment thereof and the like). Thus, a promoter nucleotide sequence is operably linked to a given DNA sequence if the promoter nucleotide sequence directs the transcription of the sequence.

Similarly, the phrase "under transcriptional control" means that the promoter is in the correct location and orientation in relation to the nucleic acid to control RNA polymerase initiation and expression of the gene. Any promoter that—will drive the expression of the nucleic acid may be used. The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter. Common promoters include, e.g., the human cytomegalovirus (CMV) immediate early gene promoter, the SV40 early promoter, the Rous sarcoma virus long terminal repeat, [beta]-actin, rat insulin promoter, the phosphoglycerol kinase promoter and glyceraldehyde-3-phosphate dehydrogenase promoter, all of which are promoters well known and readily available to those of skill in the art, can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient to produce a recoverable yield of protein of interest. By employing a promoter with well known properties, the level and pattern of expression of the protein of interest following transfection or transformation can be optimized. Inducible promoters also may be used.

Another regulatory element that is used in protein expression is an enhancer. These are genetic elements that increase transcription from a promoter located at a distant position on the same molecule of nucleic acid. Where an expression construct employs a cDNA insert, one will typically desire to include a polyadenylation signal sequence to effect proper polyadenylation of the gene transcript. Any polyadenylation signal sequence recognized by cells of the selected transgenic animal species is suitable for the practice of the invention, such as human or bovine growth hormone and SV40 polyadenylation signals.

Nucleic Acids, Vectors and Host Cells of the Invention

A second object of the invention relates to a nucleic acid sequence encoding a polypeptide of the invention for use in the treatment or prevention of an inflammatory disease.

In a particular embodiment of the invention, said inflammatory disease is an inflammatory bowel disease.

As used herein, said nucleic acid sequence may be a DNA or a RNA sequence.

In a preferred embodiment, said nucleic acid sequence encodes a polypeptide comprising or consisting of the nucleic acid sequence SEQ id n°:2.

As used herein, said nucleic acid sequence encompasses derivatives or fragments thereof. Preferably, said derivatives or fragments are conservative derivatives or fragments.

In a preferred embodiment, said nucleic acid sequence, derivative or fragment thereof is isolated.

A third object of the invention relates to a vector comprising a nucleic acid sequence of the invention for use in the treatment or prevention of an inflammatory disease.

In a particular embodiment of the invention, said inflammatory disease is an inflammatory bowel disease.

The term "vector" (or "cloning vector" and "expression vector") means the vehicle by which a nucleic acid sequence can be introduced into a host cell, so as to transform the host and promote expression (e.g. transcription and translation) of the introduced sequence.

Typically, a nucleic acid sequence of the invention may be included in any suitable vector, such as a plasmid, cosmid, episome, artificial chromosome, phage or a viral vector.

Such vectors may comprise regulatory elements, such as a promoter, enhancer, terminator and the like, to cause or direct expression of said polypeptide upon administration to a subject. Examples of promoters and enhancers used in the expression vector for animal cell are well known in the art and include early promoter and enhancer of SV40, LTR promoter and enhancer of Moloney mouse leukemia virus, promoter and enhancer of immunoglobulin H chain and the like.

According to the invention, any expression vector for animal cell can be used, so long as a nucleic acid sequence of the invention can be inserted and expressed. Examples of suitable vectors include pAGE107, pAGE103, pHSG274, pKCR, pSG1 beta d2-4 and the like.

Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO94/19478.

A fourth object of the present invention relates to a host cell which has been transfected, infected or transformed by a nucleic acid sequence and/or a vector of the invention for use in the treatment or prevention of an inflammatory disease.

In a particular embodiment of the invention, said inflammatory disease is an inflammatory bowel disease.

The term "transformation" means the introduction of a "foreign" nucleic acid sequence to a host cell, so that the host cell will express the introduced sequence to produce a desired substance, typically a polypeptide encoded by the introduced sequence. A host cell that receives and expresses introduced DNA or RNA bas been "transformed".

Examples of host cells that may be used for the invention are well known in the art, and some of them are described above.

In a particular embodiment of the invention, said host cell may be a probiotic.

Said probiotic is a is a host cell, generally a bacterium or yeast cell, which has been transfected, infected or transformed by a nucleic acid sequence and/or a vector of the invention.

Examples of host cells that can be used comprise, but are not limited to, *Bacillus coagulans, Bifidobacterium animalis, Bifidobacterium longum, Lactobacillus acidophilus, Lactobacillus paracasei, Lactobacillus johnsonii, Lactobacillus plantarum, Lactobacillus reuteri, Lactobacillus reuteri Protectis, Saccharomyces boulardii, Lactobacillus rhamnosus, Lactobacillus acidophilus, Lactobacillus bulgaricus,* and *Streptococcus thermophilus.*

Vectors and host cells of the invention are adapted to an administration in patients, preferably humans. One skilled in the art can easily choose such vectors and host cells.

In one embodiment, the invention relates to a nucleic acid, vector or host cell of the invention for use as an anti-inflammatory drug.

According to the invention, the nucleic acid sequence, vector and host cell of the invention may be used to produce a recombinant polypeptide of the invention in a suitable expression system.

Pharmaceutical Compositions and Therapeutic Methods of the Invention

A fifth object of the invention relates to a pharmaceutical compositions comprising a polypeptide of the invention, a nucleic acid sequence of the invention, a vector of the invention or a host cell of the invention and a pharmaceutically acceptable carrier.

In one embodiment, the invention relates to said pharmaceutical composition for the treatment of inflammatory disease.

In a more particular embodiment of the invention, said inflammatory disease is an inflammatory bowel disease.

The term "pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The polypeptide, nucleic acid sequence, vector or host cell of the invention may be combined with pharmaceutically acceptable excipients, and optionally sustained-release matrices, such as biodegradable polymers, to form therapeutic compositions.

In general, polypeptide, nucleic acid sequence, vector or host cell of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral, using a convenient daily dosage regimen which can be adjusted according to the degree of affliction.

A polypeptide, nucleic acid sequence, vector or host cell of the present invention, together with one or more conventional adjuvants, carriers, or diluents, may be placed into the form of pharmaceutical compositions and unit dosages. The pharmaceutical compositions and unit dosage forms may comprise conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The polypeptide, nucleic acid sequence, vector or host cell of the present invention may be formulated in a wide variety of oral administration dosage forms. The pharmaceutical compositions and dosage forms may comprise a polypeptide, nucleic acid sequence, vector or host cell of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, gum tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents.

Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The polypeptide, nucleic acid sequence, vector or host cell of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents.

Alternatively, the active ingredient may be in powder form, obtained by aseptic isolation of sterile solid or by lyophilization from solution for constitution before use with a suitable vehicle, e.g., sterile, pyrogen-free water.

The polypeptide, nucleic acid sequence, vector or host cell of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or gum tragacanth; pastilles comprising the active ingredient in an inert base such as gelatin and glycerin or sucrose and acacia; and mouthwashes comprising the active ingredient in a suitable liquid carrier.

The polypeptide, nucleic acid sequence, vector or host cell of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The polypeptide, nucleic acid sequence, vector or host cell of the present invention may be formulated for vaginal administration.

Pessaries, tampons, creams, gels, pastes, foams or sprays containing in addition to the active ingredient such carriers as are known in the art to be appropriate.

The polypeptide, nucleic acid sequence, vector or host cell of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The polypeptide, nucleic acid sequence, vector or host cell of the present invention may be formulated for aerosol administration, particularly to the respiratory tract and including intranasal administration. The compound will generally have a small particle size for example of the order of five (5) microns or less.

Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, nitrogen, nitrous oxide, carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support.

Other pharmaceutically acceptable forms include, e.g. tablets or other solids for oral administration; time release capsules; and any other form currently used. Non degradable capsules, or gastro-resistant capsules may also be used. Such pharmaceutical forms are well known in the art.

In certain embodiments, the use of liposomes and/or nanoparticles is contemplated for the administration of polypeptide, nucleic acid sequence, vector or host cell of the present invention. Liposomes are particularly suitable for an oral administration of a hydrophobic compound. The formation and use of liposomes and/or nanoparticles are known to those of skill in the art.

In the particular embodiment of the treatment of an inflammatory bowel disease, more particularly Crohn's disease, an oral or a rectal administration are preferred. For oral administration, gastro-resistant, non degradable and time release capsules are preferred.

In the particular embodiment of a composition of the invention comprising a host cell of the invention which is a probiotic, the composition may be used by oral administration.

In general, the polypeptide, nucleic acid sequence, vector or host cell of the present invention will be administered in a therapeutically effective amount by any of the accepted modes of administration for agents that serve similar utilities. Suitable dosage ranges are typically about 1-500 mg daily, preferably about 1-100 mg daily, and most preferably about 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

A sixth object of the invention relates to a method for preventing or treating an inflammatory disease in a patient in need thereof, said method comprising the step of administrating said patient with therapeutically effective amount of a polypeptide, a nucleic acid sequence a vector or a host cell of the invention.

In a particular embodiment of the invention, said inflammatory disease is an inflammatory bowel disease.

The term "patient" refers to any subject, preferably a human, afflicted with or susceptible to be afflicted with an inflammatory disease.

The terms "effective amount" and "therapeutically effective amount" refer to a sufficient amount of the agent to provide the desired biological result at a reasonable benefit/risk ratio applicable to any medical treatment. That result can be prevention, reduction and/or alleviation of the signs, symptoms, or causes of a disease, or any other desired alteration of a biological system having or at risk of having such signs, symptoms, or disease. An appropriate "effective" amount in any individual case may be determined by one of ordinary skill in the art using routine experimentation.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Food Compositions and Therapeutic Methods of the Invention

A seventh object of the invention relates to a food composition comprising a polypeptide of the invention, a nucleic acid sequence of the invention, a vector of the invention or a host cell of the invention and a dairy matrix.

In one embodiment, the invention relates to said food composition for the treatment of inflammatory disease.

In a more particular embodiment of the invention, said inflammatory disease is an inflammatory bowel disease.

The term "dairy matrix" (MXT) refers to any product containing milk, e.g. cream, homogenized milk, buttermilk, butter, yoghurt, cheese etc. Milk can be obtained from cattle, buffaloes, goats, sheep, horses, donkeys, yaks, camels or reindeers.

In general, host cell of the present invention expressing either endogenous or exogenous SlpB protein on their surface are used to produce new fermented dairy products. The preferred fermented dairy products are cheese. The more preferred fermented dairy products are monoxenic cheese, i.e. cheese matrices fermented by a unique bacteria used as unique dairy starter strain.

The food compositions may also contain food additives, and other ingredients functionally necessary for the processing. According to GENERAL STANDARD FOR FOOD ADDITIVES CODEX STAN 192-1995 of the Codex Alimentarius, the term "food additives" means any substance not normally consumed as a food by itself and not normally used as a typical ingredient of the food, whether or not it has nutritive value, the intentional addition of which to food for a technological (including organoleptic) purpose in the manufacture, processing, preparation, treatment, packing, packaging, transport or holding of such food results, or may be reasonably expected to result (directly or indirectly), in it or its by-products becoming a component of or otherwise affecting the characteristics of such foods. The term does not include contaminants or substances added to food for maintaining or improving nutritional qualities.

The food compositions may be employed as solids, such as bakery products, cheese, dry milk, semi-solids such as yoghurt, butter, cream, or liquids such as milk. Formulations containing about $10^9$ CFUs of host cells of the present invention per 1000 mg of food composition, or more broadly, about $10^8$ to about $10^{10}$ CFUs of host cells of the present invention per 1000 mg of food composition are accordingly suitable for the purpose of the invention.

The food compositions may be consumed raw or diluted in appropriate liquid for intragastric alimentation. As appropriate liquid is intended water or oil extracted from vegetal or fish.

The food compositions provide new functional fermented product for preclinical and clinical studies aimed at prevention or treatment of inflammatory bowel disease.

Method for the Screening of Bacteria having Immunomodulatory Properties

An eighth object of the invention relates to a method for the screening of bacteria having immunomodulatory properties comprising the step of:

a) Culturing a bacterium in a medium comprising sodium lactate and casein hydrolysate,
b) Preparing a protein sample extract from the bacterium of step a),
c) Measuring the expression level of the polypeptide comprising or consisting of the amino acid sequence SEQ id n°:1, a conservative derivative or a fragment thereof, in the protein sample extract as prepared in step b), and
d) Selecting the bacteria expressing said polypeptide as defined in step c).

In the context of the invention, the term "immunomodulatory properties" refers to the ability of modulating the action of immune cells. By "immune cells" are intended cells of the immune system. Such cells share specific mechanisms such as phagocytosis, lysis and cytokines synthesis. Preferably, the bacteria targeted by the method of screening according to the invention are those able to interfere with one of these mechanisms. More specifically, the bacteria targeted by the method of screening according the invention are those able to interfere with cytokines synthesis, and notably with interleukins synthesis. Interleukins may have either pro- or anti-inflammatory properties on cells involved in inflammatory diseases. In the context of the present invention, the bacteria having immunomodulatory properties may either increase the synthesis of anti-inflammatory interleukins or decrease the synthesis of pro-inflammatory interleukins.

Preferably, the bacteria are cultured in a medium comprising nutrients suitable for their growth. The bacteria identified by the screening method according to the invention may use different carbon and energy sources, ie—carbohydrates such as lactose, or lactate. These bacteria may also use different nitrogen sources, i.e.—peptone, amino-acids, mineral nitrogen. Particularly, said medium comprises sodium L-lactate and casein hydrolysate. The addition of sodium L-lactate in the media facilitates the growth of bacteria. The addition of casein hydrolysate allows reduction the generation time. These compounds fulfill the nutritional requirements of bacteria, notably concerning nitrogen and carbon.

In a particular embodiment of the invention, the concentrations of sodium L-lactate and casein hydrolysate in the medium used to culture bacteria according to the method for the screening of bacteria having immunomodulatory properties are respectively 50 mM and 5 g/L.

In a more particular embodiment of the invention, the bacterium of step a) is a propionibacterium cultured in a medium appropriate for its growth. As an example, such an appropriate medium may be YEL, molasses, whey or any other suitable medium well known by the skilled person.

Since the polypeptide comprising or consisting of the amino acid sequence SEQ id n°:1, a conservative derivative or a fragment thereof, belongs to the family of surface proteins non-covalently associated to the cell wall, the protein sample extract resulting from the cultured bacterium of step a) is prepared in the presence of a compound able to disrupt binding between said polypeptide and the cell wall of bacterium. This type of compounds is well known by the skilled person. As an example, said compound may be guanidine hydrochloride. In a particular embodiment of the method according to the invention, the protein sample extract of step b) is obtained by incubating the bacteria cultured in step a) in a solution comprising guanidine hydrochloride. Preferably, the concentration of the guanidine hydrochloride used in the solution to prepare protein sample extract varies between 4M to 8M.

In the context of the method of the invention, the term "measuring the expression level" of the polypeptide comprising or consisting of the amino acid sequence SEQ id n°:1, a conservative derivative or a fragment thereof refers to the ability to detect its presence within the mixture of proteins of the protein sample extract. The detection of the presence of the polypeptide can be done by several means, all well known by the skilled person.

Preferably, the expression level of the polypeptide comprising or consisting of the amino acid sequence SEQ id n°:1, a conservative derivative or a fragment thereof, may be detected by using a specific antibody.

In a particular embodiment of the invention, the expression level of the polypeptide comprising or consisting of the amino acid sequence SEQ id n°:1, a conservative derivative or a fragment thereof, may be detected by using mass spectroscopy.

The following examples describe some of the preferred modes of making and practicing the present invention. However, it should be understood that the examples are for illustrative purposes only and are not meant to limit the scope of the invention.

EXAMPLES

1) Prediction of Subcellular Localization of the Predicted Proteins.

Analysis of the draft genomic sequence of the *P. freudenreichii* ITG P20 strain revealed 2324 predicted protein-coding genes. This number is close to that in the type strain CIRM-BIA $1^T$, the first publically available sequenced genome of *P. freudenreichii*, which contained 2439 protein-coding genes.

2) Extraction and Analysis of Surface Proteins Non-Covalently Associated to the Cell Wall.

*P. freudenreichii* strain ITG P20, also called CIRM-BIA 129, was provided by the CIRM-BIA Biological Resource Center (Centre International de Ressources Microbiennes-Bactéries d'Intérêt Alimentaire, INRA, Rennes, France). It was cultivated at 30° C. without shaking in cow milk ultrafiltrate supplemented with 50 mM of sodium L-lactate (GALAFLOW SL60, ARNAUD) and 5 g/L of casein hydrolysate (ORGANOTECHNIE), sterilized by 0.2 μm filtration (NALGENE). Milk ultrafiltrate was produced using a UF pilot equipment (T.I.A) equipped with organic spiral membrane with a molecular weight cut-off of 5 kDa (KOCH INTERNATIONAL). Growth was monitored spectrophotometrically at 650 nm ($OD_{650}$), as well as by counting colony-forming units (CFU) in YEL medium containing 1.5% agar. 100 ml of stationary phase culture of bacteria were harvested in stationary phase (76 hours, $10^9$ CFU/mL) by centrifugation (6 000×g, 10 min, 4° C.), and washed in an equal volume of PBS prior to resuspension in 5M guanidine hydrochloride to a final $OD_{650}$ of 20. The suspension was incubated 15 min at 50° C. prior to centrifugation (21 000×g, 20 min, 30° C.) to eliminate cells. The supernatant was then dialyzed exhaustively against 0.1% SDS in distilled water during 24 h at 4° C. using 10,000 kDa cutoff Slide-A-Lyer® Dialysis Cassette (THERMOSCIENTIFIC) prior to proteomic investigations.

The obtained proteins were analyzed on SDS PAGE as compared to whole-cell protein extract and to culture supernatant.

The FIG. 1 shows a whole-cell protein extract (line 1), the culture supernatant (line 2) and a Guanidine hydrochloride extract (line 3) separated on 10% SDS PAGE.

This electrophoretic analysis revealed the presence of five protein bands in the guanidine extract (FIG. 1, lane 3). The gel lane number 3 was sliced and all the strips were subjected to in-gel trypsin digestion followed by nano-LC-MS/MS analysis.

Five proteins, indicated in the corresponding gel zones in FIG. 1, were clearly identified by MS/MS with 3 to 34 unique peptides. These were internalin A (InlA), large surface protein A (lspA), surface protein with SLH Domain E (slpE), surface layer protein slpA and slpB.

The major surface layer protein, SlpB, was further characterized using LC-MS for accurate molecular mass determination. It was separated by reverse phase chromatography and the major peak (elution time 31 minutes) gave a clear MS signal. The corresponding raw MS spectrum showing a single protein charge state envelope allowed reconstruction of a deconvoluted mass spectrum. The deduced average molecular weight of this protein was 54,147 Da, with an accuracy of +/−5Da, considering the thirty most intense charge states of the protein visible on the mass spectrum. This mass did not correspond with any of the one predicted for the 5 proteins identified in this extract. However, a 29 residues long signal peptide was predicted using the PHO-BIUS tool (Stockholm Bioinformatics Centre) in the 556 residues slpB gene sequence (See in FIG. 2). The resulting 527 residues processed protein had a theoretical mass of 54,145 Da, which is compatible with the 54,147 Da experimental mass, considering the accuracy of the spectrometric measure. This confirms that processed slpB is the main protein in the guanidine extract of *P. freudenreichii* ITG P20.

3) Immunomodulatory properties of surface proteins non-covalently associated to the cell wall.

A guanidine hydrochloride preparative extraction was performed on *P. freudenreichii* ITG P20. The immunomodulatory properties of the extract were evaluated on human PBMCs, in comparison with intact propionibacteria.

Figure 3:
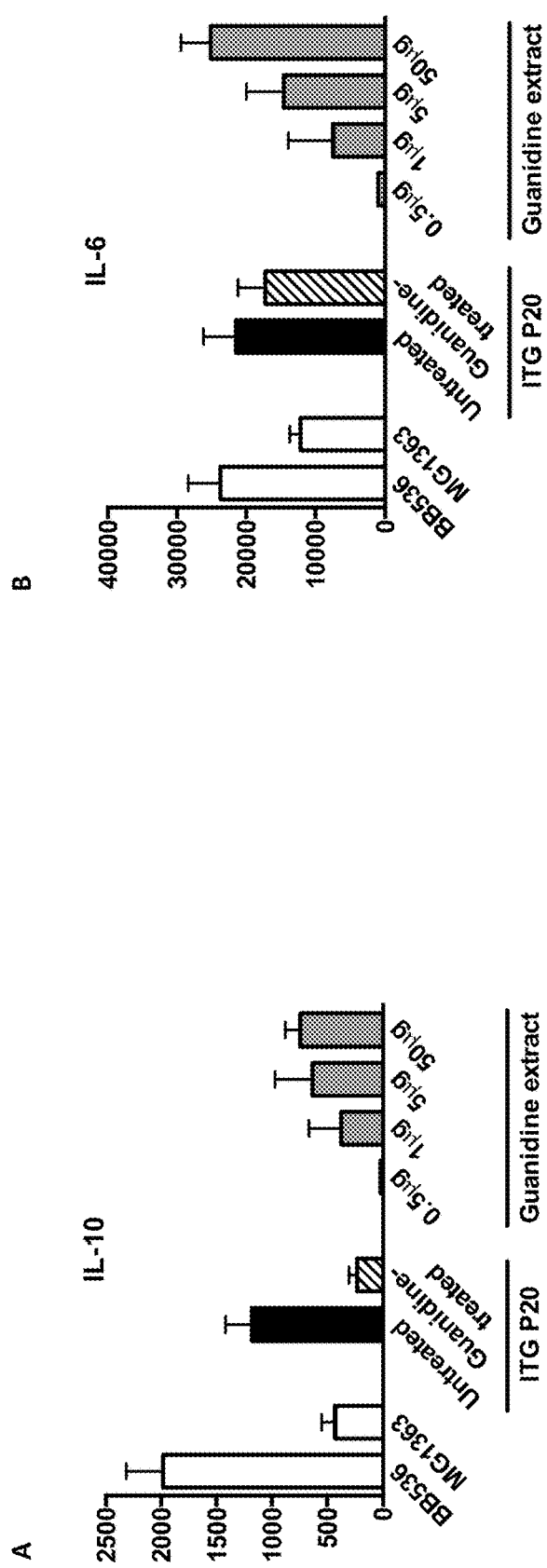
FIG. 3 shows the IL-6 and IL-10 production of PBMC contacted with Guanidine hydrochloride extract of *P. freudenreichii*.

Peripheral Blood Mononuclear Cells were isolated from blood of three healthy donors and reference bacterial strains were prepared as previously described (FOLIGNE et al., *World J Gastroenterol.*, vol. 13 (2), 236-243, 2007). Propionibacteria were harvested from fermented milk ultrafiltrate and were either guanidine-extracted (as described above) or left untreated. Propionibacteria, extracted or not, were washed in PBS and resuspended in PBS containing 20% glycerol at the same density (turbidimetry Mc Farland unit 3, as previously described). They were then added to PBMCs at a propionibacteria-to-immune cell ratio of 5. Finally, a *P. freudenreichii* guanidine hydrochloride surface protein extract (see above) was extensively dialyzed against PBS, proteins were quantified using the Bradford Assay. Different amounts (0.5 to 50 μg, see FIG. 3) of extracted surface proteins were then added to PBMCs. After 24-h stimulation, culture supernatants were collected, clarified by centrifugation and stored at −20° C. until cytokine analysis. These were quantified by ELISA using antibodies provided by R&D systems, for IL-6 and TNF-α or by BD Pharmingen for IL-10, IL-12 and IFN-γ.

The FIGS. 3A and B show the production of IL-10 and IL-6 respectively by human peripheral blood mononuclear cells (PBMCs) in response to stimulation with reference bacteria *Bifidobacterium longum* BB536 and *Lactococcus lactis* MG1363 (white bars), with *Propionibacterium freudenreichii* ITG P20, either untreated (black bars) or guanidine-treated (hatched bars), or with 0.5, 1.0, 5.0 and 50 μg of guanidine-extracted proteins (grey bars). Data are expressed in pg/ml as mean±SEM (n=3 healthy donors).

Figure 4:
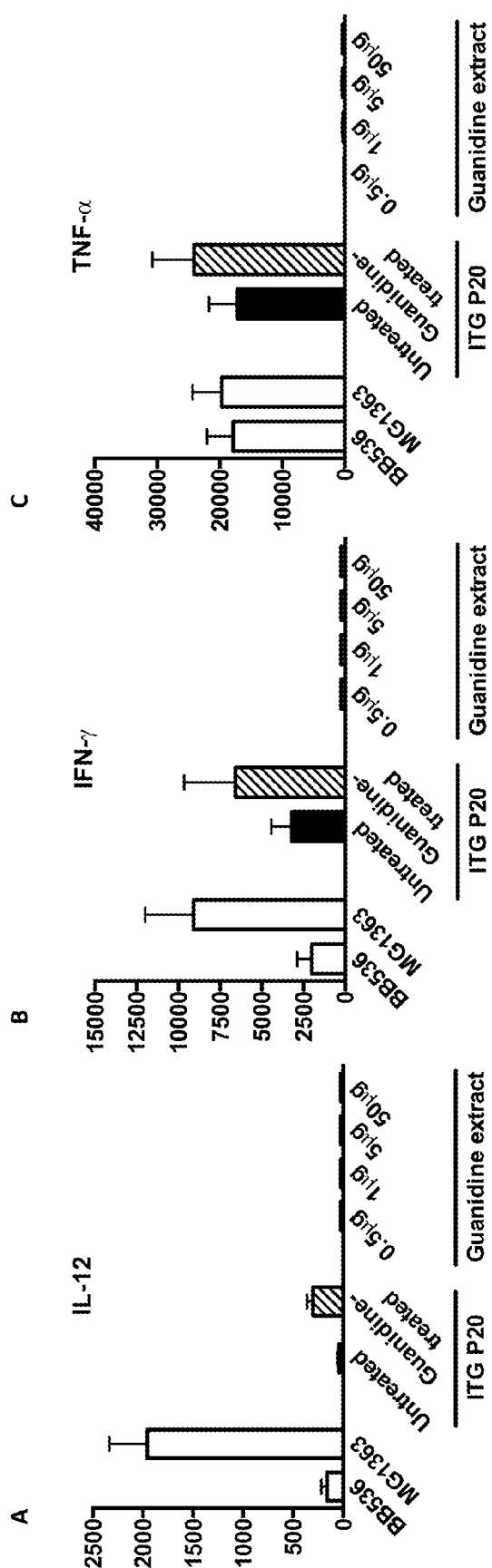
FIG. 4 shows the IL-12, IFN-γ and TNF-α production of PBMC contacted with Guanidine hydrochloride extract of *P. freudenreichii*.

The FIGS. 4A, B and C show the production of IL-12, IFN-γ and TNF-α respectively by human peripheral blood mononuclear cells (PBMCs) in response to stimulation with reference bacteria *Bifidobacterium longum* BB536 and *Lactococcus lactis* MG1363 (white bars), with *Propionibacterium freudenreichii* ITG P20, either untreated (black bars) or guanidine-treated (hatched bars), or with 0.5, 1.0, 5.0 and 50 μg of guanidine-extracted proteins (grey bars). Data are expressed in pg/ml as mean±SEM (n=3 healthy donors).

The results established that the guanidine surface protein extract induced release of IL-10 and IL-6, in a dose-dependent manner (FIGS. 3A & B), with little or no effect on IL-12, TNF-α and IFN-γ (FIG. 4A to C), in human PBMCs. As a comparison, intact *P. freudenreichii* ITG P20 cells induced release of the 4 cytokines, IL-10, IL-6, TNF-α and IFN-γ. However, guanidine-treated *P. freudenreichii* ITG P20 lost the ability to induce IL-10. This indicates that the surface extractable proteins trigger the release of the immunomodulatory cytokines IL-10 and IL-6. As a control, same amounts of bovine serum albumin were tested and induced no cytokine secretion in PBMCs (data not shown).

In a second experiment, PBMCs were stimulated by the pro-inflammatory *Lactococcus lactis* MG1363, by the guanidine *P. freudenreichii* surface protein extract, or by the combination thereof.

Figure 5:
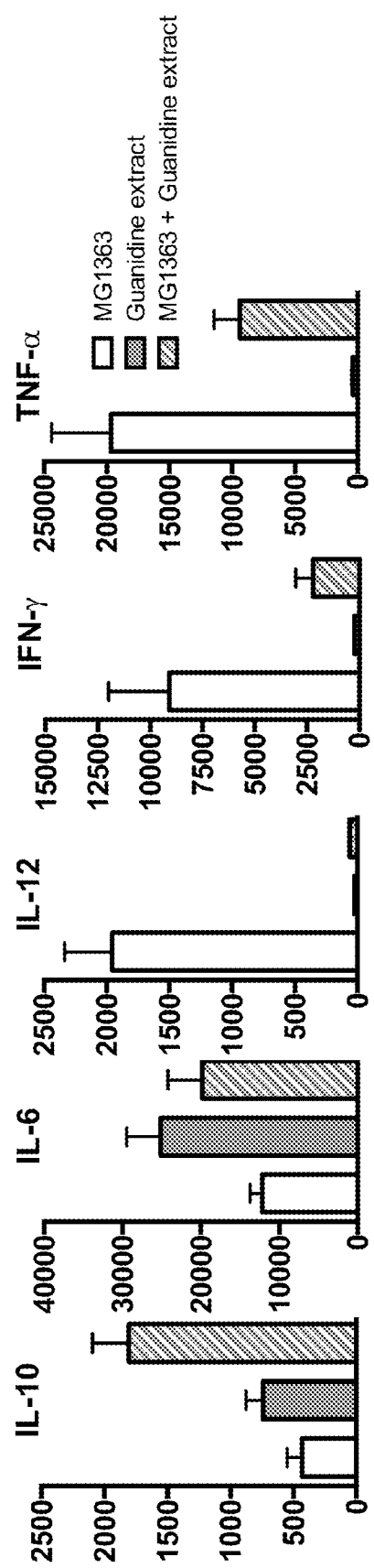
FIG. 5 shows the IL-6, IL-10, IL-12, IFN-γ and TNF-α production of PBMC contacted with Guanidine hydrochloride extract of *P. freudenreichii* in conjunction, or not, with *Lactococcus lactis* MG1363.

The FIG. 5 shows the production of cytokines by human PBMCs in response to *L. lactis* MG1363 (white bars), 50 μg of extracted proteins (grey bars), or the combination thereof (hatched bars). Data are expressed in pg/ml as mean±SEM (n=3 healthy donors).

The results established that *L. lactis* induced secretion of the pro-inflammatory cytokines IL-12, IFN-γ and TNF-α. By contrast, the guanidine extract induced IL-10 and IL-6 secretion. Moreover, this extract, when applied in conjunction with the pro-inflammatory *L. lactis*, drastically reduced induction of the pro-inflammatory cytokines IL-12, IFN-γ and TNF-α by this bacterium. This confirms the immunomodulatory effect of *P. freudenreichii* surface proteins, with a marked anti-inflammatory profile.

4) Focus on Surface Accessibility of Two Key Proteins

We used the peptides detected by shaving (i.e. released from bacterial cells by trypsin digestion of live *P. freudenreichii* cells) to specify the surface topology of splB and identify the exposed domains, most likely to interact with the host.

S-layer proteins are reportedly involved in adhesion and immunomodulation in other bacteria. They are anchored to cell wall via electrostatic interactions involving SLH domains and pyruvylated cell wall polymers.

The FIG. 2 shows the aminoacid sequence of slpB and surface accessibility. The signal sequence is underlined. The potent trypsin cleavage sites are indicated by dark triangles following lysine (K) and arginine residues (R). The peptides detected in the shaving extracellular fraction are highlighted, evidencing the surface-accessible cleavage sites. The 3 SLH domains detected in slpB are indicated.

As indicated in FIG. 2, extracellular released peptides covered 49% of *P. freudenreichii* slpB protein, showing great surface accessibility of the N-terminal part, except for the cleavable signal sequence. By contrast, the C-terminal region, containing 3 predicted SLH domains, was poorly represented. This confirms the hypothesis that slpB SLH domains are embedded in the peptidoglycan thick layer, thus not accessible to the enzyme 5) Implication of the SlpB Proteins in the Immunomodulatory Properties Data acquired using both the ITG P20/CIRM BIA 129 strain of *P. freudenreichii* and the dialyzed guanidine extract strongly suggested the implication of SlpB in the immunomodulatory properties of the strain.

To confirm this hypothese, the corresponding slpB gene was mutated by insertional inactivation as previously described (DEUTSCH et al., *Appl. Environ. Microbiol.*, vol. 76 (9), 2740-2746, 2010). Briefly, a suicide vector was constructed by inserting a chloramphenicol resistance gene in a pUC18 plasmid. In the resulting plasmid, an internal fragment of 574-bp of the slpB (SEQ id n°3) Open Reading Frame (ORF) of the strain CIRM-BIA129 was cloned, resulting in the vector pUC:slpB:CmR.

The strains of *P. freudenreichii* to be tested were transformed with this vector and transformants harbouring inserted pUC:slpB:CmR were selected on YEL agar medium with chloramphenicol. The stability of the insertion was checked in YEL without chloramphenicol. Insertional inactivation of the slpB gene was verified by PCR amplification of the corresponding locus.

Figure 6:
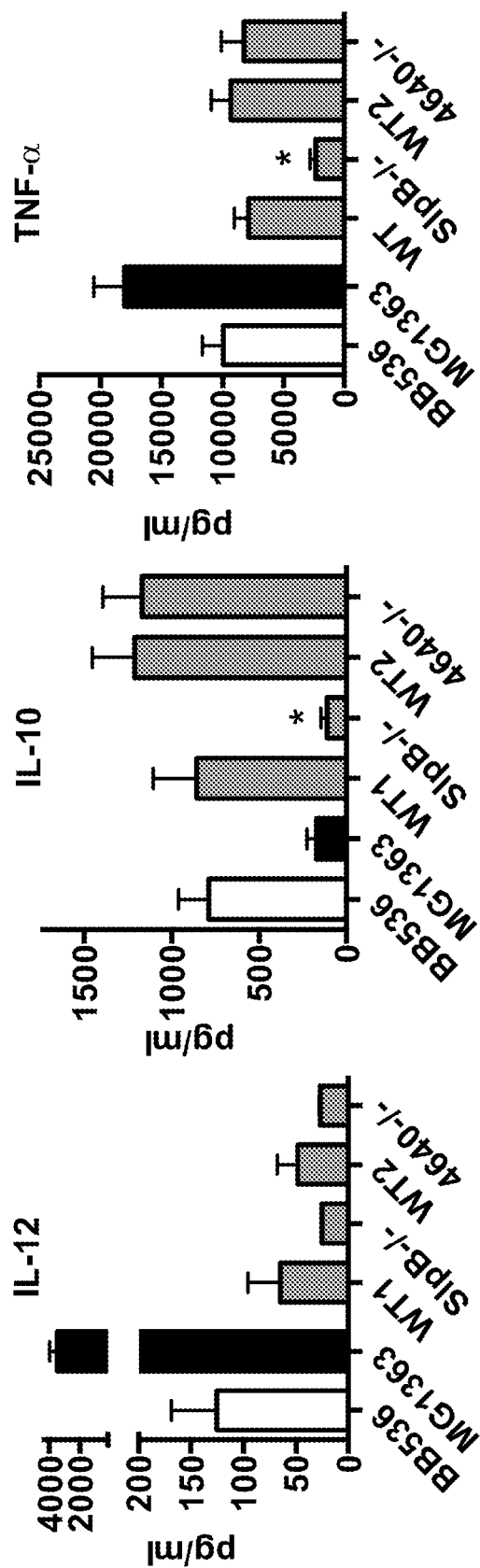
FIG. 6 shows the IL-12, IL-10 and TNF-α production of PBMC contacted with *P. freudenreichii* deleted or not from the slpB gene expression.

The FIG. 6 shows the production of cytokines by human peripheral blood mononuclear cells (PBMCs) in response to bacteria, wild type or mutated. Cytokines were assessed by ELISA in the supernatants collected from 24 h cultures of human PBMCs. As a comparison, a strain mutated in a protein of unknown function, Pouf 4640, was also tested.

The resulting mutant was compared to the wild type strain with respect to cytokine induction in human PBMCs. As shown in FIG. 6, inactivation of the slpB gene (slpB−/−) led to drastic reduction of the level of induced cytokines. By contrast, inactivation of the Pouf 4640 (4640−/−) gene had little or no effect on the immunomodulatory properties of *P. freudenreichii*.

In conclusion, we have demonstrated that splB is a key factor of the immunomodulation *P. freudenreichii*.

6) Pre-Clinical Study of Anti-Inflammatory Effect of SlpB Protein In Vivo 6.1—Bacterial Growth and Starter Production

*P. freudenreichii* strain ITG P20, also called CIRM-BIA 129, was provided by the CIRM-BIA Biological Resource Center (Centre International de Ressources Microbiennes-Bactéries d'Intérêt Alimentaire, INRA, Rennes, France) and routinely grown in YEL medium. For starter production, it was grown in a food grade medium consisting of milk ultrafiltrate supplemented with 50 mM of sodium L-lactate (galaflow SL60, Société Arnaud, Paris, France) and 5 g/L of casein hydrolysate (Organotechnie, La Courneuve, France), sterilized by 0.2 μm filtration (Nalgene, Roskilde, Denmark) as described previously (COUSIN et al., *Journal of Agricultural and Food Chemistry*, vol. 60, 7917-7927, 2012).

6.2—Monoxenic Cheese Manufacturing

The above described starter cultures were used to inoculate (initial population $10^6$ CFU/mL) microfiltrated skimmed raw cow milk supplemented with 100 g/L milk powder (Promilk® 852B, Ingredia, France), 5 g/L casein peptone plus (Organotechnie, La Courneuve, France) and 150 g/L cream. This supplemented milk containing, per Liter, 105 g proteins, 110 g lipids and 40 g lactose, was autoclaved before inoculation. After 72 h at 30° C., final propionibacteria population was 2.50 (±0.82) $10^9$ CFU/mL with a pH of 5.5. Cheese was manufactured in sterile conditions under laminar flow: addition of coagulant (chy-max® Extra, Chr. Hansen), coagulation at 32° C., cutting of the curd, heating at 40° C. for 10 min, moulding and pressing. Pressed monoxenic cheese was then dried under laminar flow for 1 h, wrapped under vacuum in sterile ripening bags and stored at 4° C. Propionibacteria population, determined on lithium-glycerol agar as described previously (FALENTIN et al., *Food Microbiology,* vol. 29, 132-140, 2012), was 9.69 (±4.70) $10^9$ CFU/g. Contaminants, checked on plate count agar, was below 100 CFU/g. As a control, a sterile dairy matrix was prepared by using gluconodeltalactone acidification of sterile supplemented milk followed by coagulation, cutting, moulding and pressing as described above.

6.3—Experimental Colitis.

6.3.1—Animal Care and Ethical Aspects.

Female BALB/c mice (6 weeks old on arrival) were obtained from Charles River Laboratories (Saint-Germain sur l'Arbresle, France). The animals were randomly divided into groups of ten and housed in a controlled environment (with a temperature of 22° C., a 12h/12h light/dark cycle and ad libitum access to food and water). All animal experiments were performed according to the guidelines of the Institut Pasteur de Lille Animal Care and Use Committee and in compliance with the Amsterdam Protocol on Animal Protection and Welfare and Directive 86/609/EEC on the Protections of Animals Used for Experimental and Other Scientific Purposes (updated in the Council of Europe's Appendix A). The animal work was also compliant with French Legislation (the French Act 87-848, dated 19-10-1987) and the European Communities Amendment of Cruelty to Animals Act 1976). The study's objectives and procedures were approved by the Nord-Pas-de-Calais region's Ethic and Welfare Committee for Experiments on Animals (Lille, France; approval number: 19/2009R).

6.3.2—Feeding Procedure.

Both the monoxenic cheese and the corresponding sterile dairy matrix were homogenized in physiological water just before feeding. Groups of 10 mice were given either physiological water ("control mice", labelled CTL), 100 mg of the dairy matrix (MTX) or 100 mg of P *cheese containing* $10^9$ CFUs of *P. freudenreichii,* via the intragastric route. Treatments were given daily for five consecutive days.

6.3.3—TNBS-Induced Colitis and Inflammation Scoring.

Acute colitis was triggered on day 5 by intra-rectal administration of 50 µto reach 100 mg/kg bodyweight TNBS (Sigma-Aldrich, Saint-Louis, Mo., USA) in 0.9% NaCl/ethanol (50/50 v/v) (DROUAULT-HOLOWACZ et al., *Clin. Nutr.,* vol. 25, 994-1003, 2006). The animals were monitored daily for bodyweight loss. Three days after the induction of colitis, mice were sacrificed and blood samples were collected immediately. Serum was separated and frozen (−20° C.) until protein assays were performed. After dissection and colon length measure, two independent observers blindly scored the macroscopic inflammation of the colon on the Wallace scale (WALLACE et al., *Gastroenterology,* vol. 96, 29-36, 1989). Samples for histologic analysis were fixed in 4% formaldehyde, dehydrated and embedded in paraffin. 5 µm sections were stained with May-Grunwald-Giemsa reagents. Following examination under microscope, tissue lesions were scored according to the Ameho criteria (AMEHO et al., *Gut,* vol. 41, 487-493 1997). Lastly, colon segments were also removed and stored at −20° C. for further myeloperoxidase (MPO) activity assays.

6.3.4—Biomarker Analysis.

Murine IL-6 and SAA levels were measured by ELISA using commercial antibodies from BD Pharmingen (Franklin Lakes, N.J.) and Tridelta Development Ltd (Maynooth, Ireland), respectively, with a lower limit of detection of 126 pg/ml and 31 µg/ml. Lastly, the degree of polymorphonuclear neutrophil infiltration in the distal colon was assessed by quantifying MPO activity, as previously described (BRADLEY et al., *J. Invest Dermatol.,* vol. 78, 206-209, 1982). For gene expression analysis, samples of the distal colon (0.5 cm of the inflamed area) were processed in RNA stabilization solution (RNA-later, Ambion, Life Technologies, Carlsbad, Calif., USA) and stored at −80° C. for later gene expression analysis. After homogenization of samples using the FastPrep instrument (MP Biomedicals, Santa Ana, Calif., USA), total RNA was isolated using RNA spin columns (Macherey-Nagel, Hoerdt, France). Reverse transcription and real-time PCR were performed with reaction kit (High capacity cDNA RT kit) and reagents (Universal PCR Master Mix) from Applied Biosystems (Life Technologies), according to the manufacturer's instructions. The PCR reactions were performed with MX3005P Stratagene machine (Agilent Technologies, Santa Clara, Calif., USA). For the I16, Pparγ, Cox2, Hmox and Zo1 target genes, a custom gene expression assay (Taqman, Applied Biosystems) was used with commercially designed and validated primers. The housekeeping gene β-actin was run as reference gene. Recorded data were analysed using the 2-ΔΔCt calculated method and expressed as a fold-increase over the control group's values.

6.3.5—Intestinal Microbiota Analysis

The approach used is based on an optimized and standardized process developed by Genoscreen targeting V3 and V4 hypervariable regions of the 16S rDNA (Metabiote® Solutions, Lille, France). Briefly, DNA was extracted from faeces using QIAmp Fast DNA Stool kit (Qiagen, Valencia, Calif., USA) modified by Genoscreen and was quantified by fluorescence. Amplicon libraries were performed from 5 ng of extracted DNA to amplify V3 and V4 regions of the 16S rDNA and add Sample Identifier Multiplex (SIMs®) and GS FLX adaptators. After purification, each amplicons were quantified by fluorescence before being equimolary pooled to obtain the final library. Emulsion PCR was performed as recommended by the suppliers with minor modifications and pyrosequencing was carried out on a 454 Life Science Genome Sequencer FLX instrument (Roche, Basel, Switzerland). Sequencing data were then processed with the bioinformatic pipeline MetaBiote® OnLine (GenoScreen, Lille, France) starting with a pre-processing of the reads with the following parameters: (i) size not reaching 200 bases and size exceeding 600 bases; (ii) presence of ambiguous bases; (iii) average base quality score below 25; (iv) homopolymer exceeding 6 bases; (v) error in sequence of forward primer; (vi) error in sequence of reverse primer. We then used the QIIME pipeline 1.8.0 (CAPORASO et al., *Nat. Methods,* vol. 7, 335-336, 2010) to perform BLAST analysis against the reference database Greengenes (DESANTIS et al., *Applied and Environmental Microbiology,* vol. 72, 5069-5072, 2006) for taxonomic rank assignment.

6.4—Statistical Analysis

Results are expressed as the mean±standard error of the mean (SEM). Statistical analyses were performed using GraphPad Prism 6 software (GraphPad Software Inc., La Jolla, Calif., USA). Non-parametric Mann-Whitney tests were used to calculate significance levels for measurements. Values of $P<0.05$ were considered statistically significant.

6.5 Results 6.5.1—Key *P. Freudenreichii* Anti-Inflammatory Proteins are Expressed within Cheese The CIRM BIA 129 strain of *P. freudenreichii* grew well in supplemented milk and reached populations above $10^9$ CFU/mL within 72 hours. Populations close to $10^{10}$ CFU/g were reached in the final monoxenic cheese, as a result of concentration by pressing and draining of the curd. The cheese obtained showed the following features: dry matter 43 (±1.8) %, fat content 18.4 (±0.8) %, fat in dry matter 42.6 (±0.85) %, with a *P. freudenreichii* population of 9.69 (±4.70) $10^9$ CFU/g. This composition is close to that of traditional pressed cheeses.

Bacteria were successfully isolated from the cheese curd without massive lysis, nor excessive presence of casein micelles. SDS PAGE analysis further confirmed the presence of a complex cellular proteome in the bacterial pellet without massive presence of milk proteins. Enzymatic shaving was conducted, without detectable loss of viability, as recently adapted for propionibacteria (LE MARECHAL et al., *J. Proteomics.*, vol. 113C, 447-461, 2015). The guanidine extractible proteins, including InlA, slpA, slpB and slpE, previously shown to be involved in immunomodulation by *P. freudenreichii* grown in liquid cultures, were in particular detected and thus expressed in the cheese manufactured with *P. freudenreichii* strain ITG P20.

Figure 7:
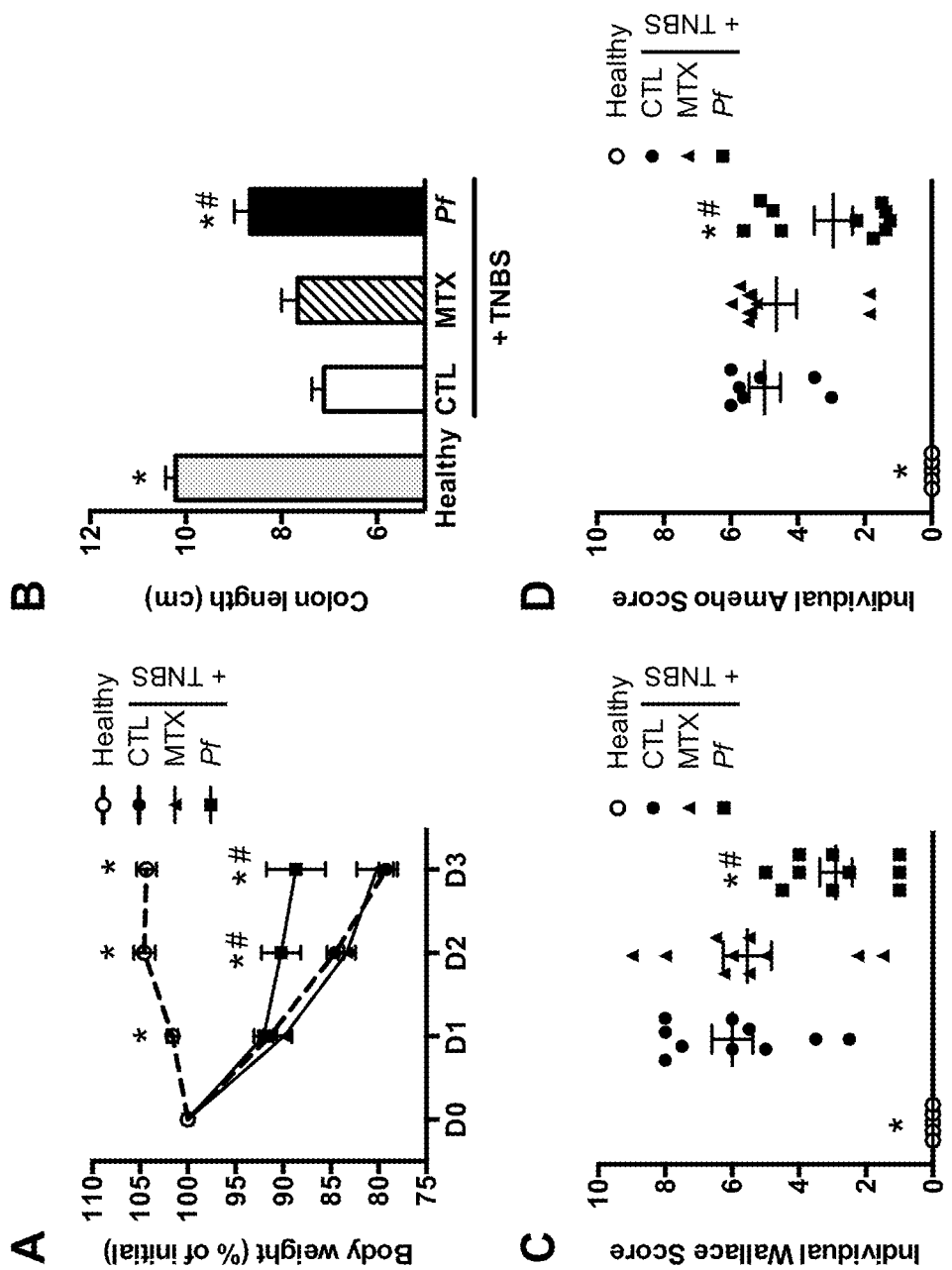
FIG. 7 shows the impact of monoxenic *P. freudenreichii* pressed cheese consumption on severity of TNBS-induced colitis. (A) Body weight loss (as a percentage of the initial weight) in the healthy, CTL, MTX and Pf groups. (B) Colon length. (C) Wallace macroscopic scores. (D) Ameho histological scores. The data represent the mean±SEM of 7 to 10 mice per group. *$p<0.05$ versus the CTL group and #$p<0.05$ versus the MTX group. (E) to (H) illustrate the colon structure of mice.
Figure 7:
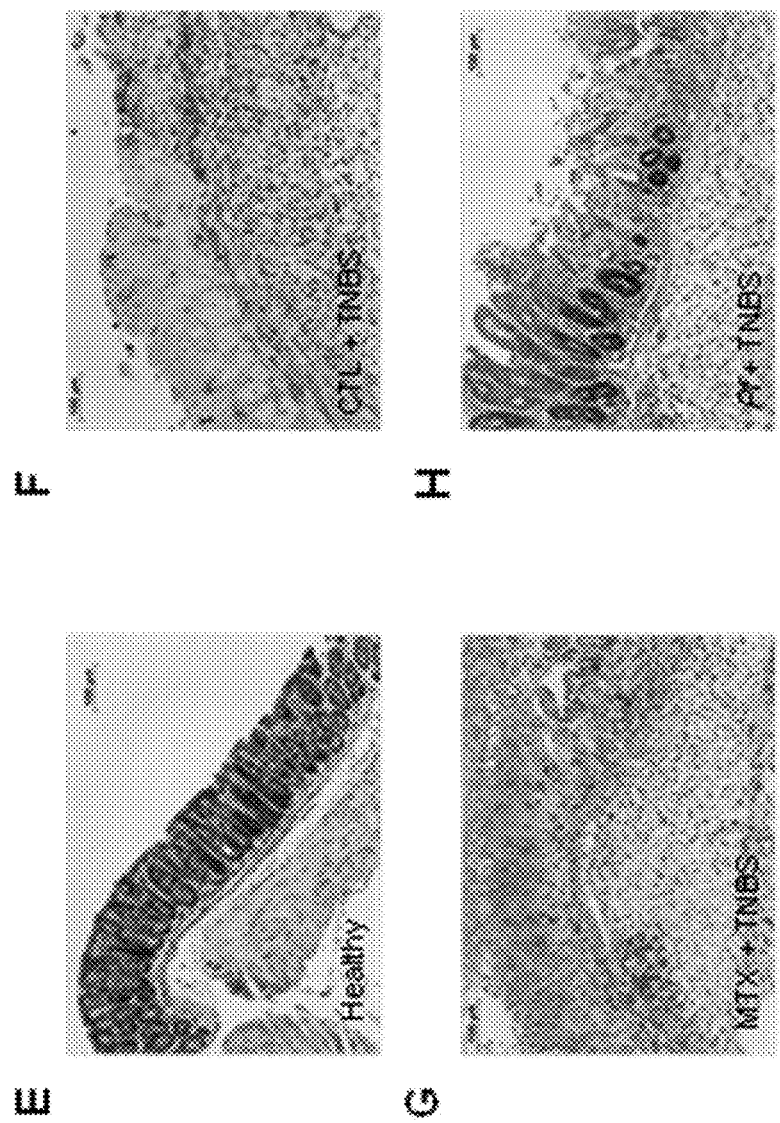

6.5.2—Monoxenic *P. Freudenreichii* Cheese, But Not Sterile Cheese, Alleviates TNBS-Induced Colitis in Mice TNBS-induced colitis led to mortality in CTL and MTX groups. In contrast, consumption of cheese fermented by *P. freudenreichii* CIRM BIA 129 (Pf) protected mice against mortality (data not shown). Pf cheese intake also restricted the body weight loss (FIG. 7A) and significantly improved Wallace (FIG. 7C) and Ameho (FIG. 7D) scores when compared to physiological water (CTL) or sterile dairy matrix (MTX) intake. In the histology, typical epithelial feature containing crypts can be shown in FIG. 7E (black coloration). TNBS-induced colitis led to disruption and necrosis of the epithelium and to important neutrophil granulocytes infiltration (FIG. 7F). Sterile dairy matrix (MTX) was unable to reverse the effects of TNBS (FIG. 7G). In contrast, consumption of cheese fermented by *P. freudenreichii* CIRM BIA 129 (Pf) protected mice against necrosis (FIG. 7H).

Altogether, these results showed that Pf cheese intake decreased severity of TNBS-induced colitis.

Figure 8:
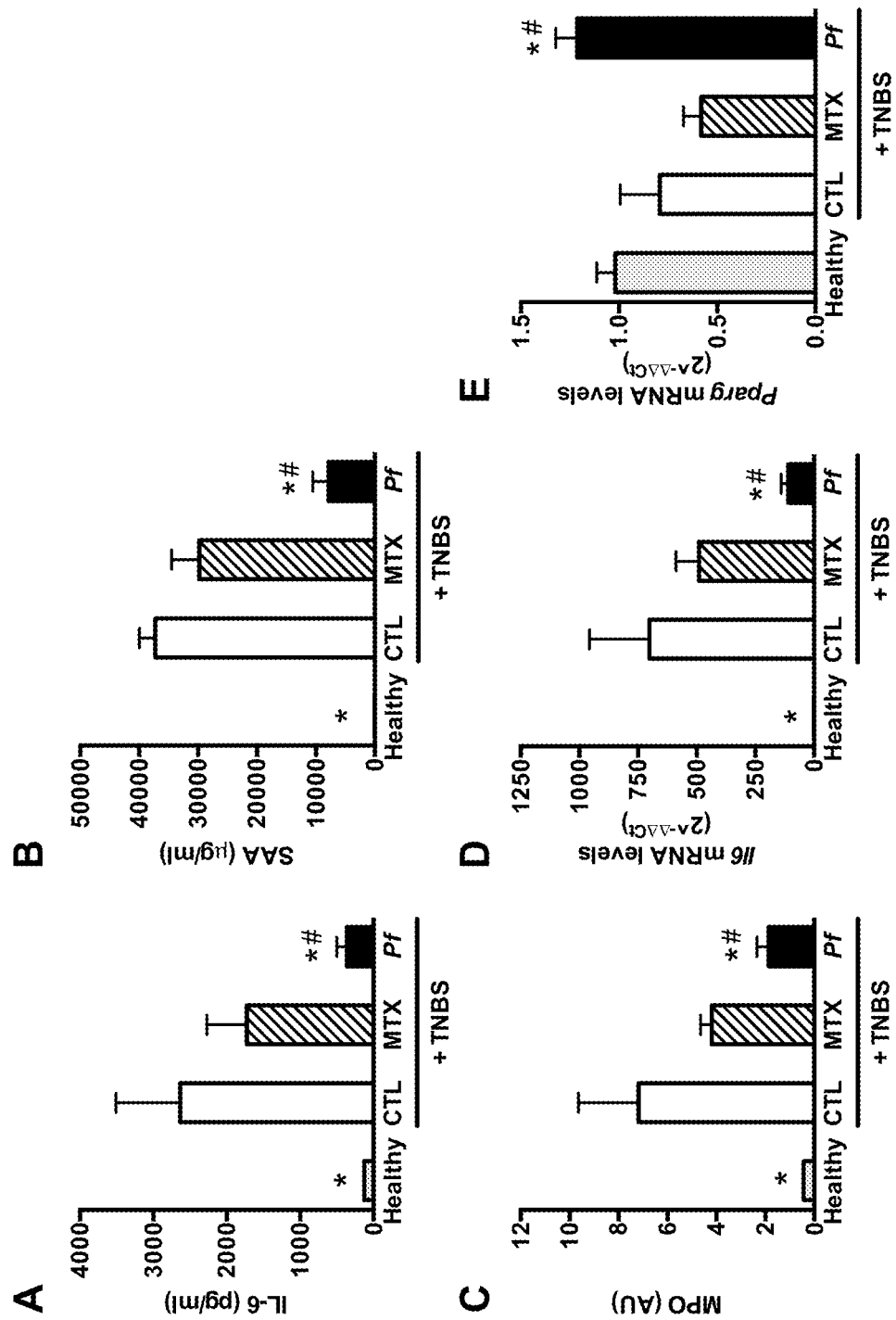
FIG. 8 shows the impact of monoxenic *P. freudenreichii* pressed cheese consumption on inflammation in TNBS-induced colitis. (A) Serum IL-6 levels in the healthy, CTL, MTX and Pf groups. (B) Serum Amyloid A (SAA) levels. (C) Colonic Myeloperoxidase (MPO) activity. (D) Colonic mRNA expression levels of Il6. (E) Colonic mRNA expression level of Ppary. The data represent the mean±SEM of 7 to 10 mice per group. *$p<0.05$ versus the CTL group and #$p<0.05$ versus the MTX group.

6.5.3—Monoxenic *P. Freudenreichii* Cheese, But Not Sterile Cheese, Modulates Local and Systemic Inflammatory Markers As shown in FIG. 8, we evaluated the degree of inflammation in blood and colon. In blood, Pf cheese intake led to a strong decrease of IL-6 and SAA levels, as compared to physiological water or MTX intake (FIGS. 8A and 8B). Furthermore, in the colon, MPO activity was significantly decreased by Pf cheese intake as compared to physiological water (CTL) or sterile diary matrix (MTX) intake (FIG. 8C). Besides MPO activity, mRNA expression levels of Il6 was strongly decreased in the Pf cheese group as compared to CTL and MTX groups (FIG. 8D). Finally, this decrease of inflammation marker level in colon was associated with an increase of Pparγ mRNA expression level in Pf cheese group compared to CTL and MTX groups (FIG. 8E). Collectively, Pf cheese intake protected mice against inflammation induced by TNBS.

Figure 9:
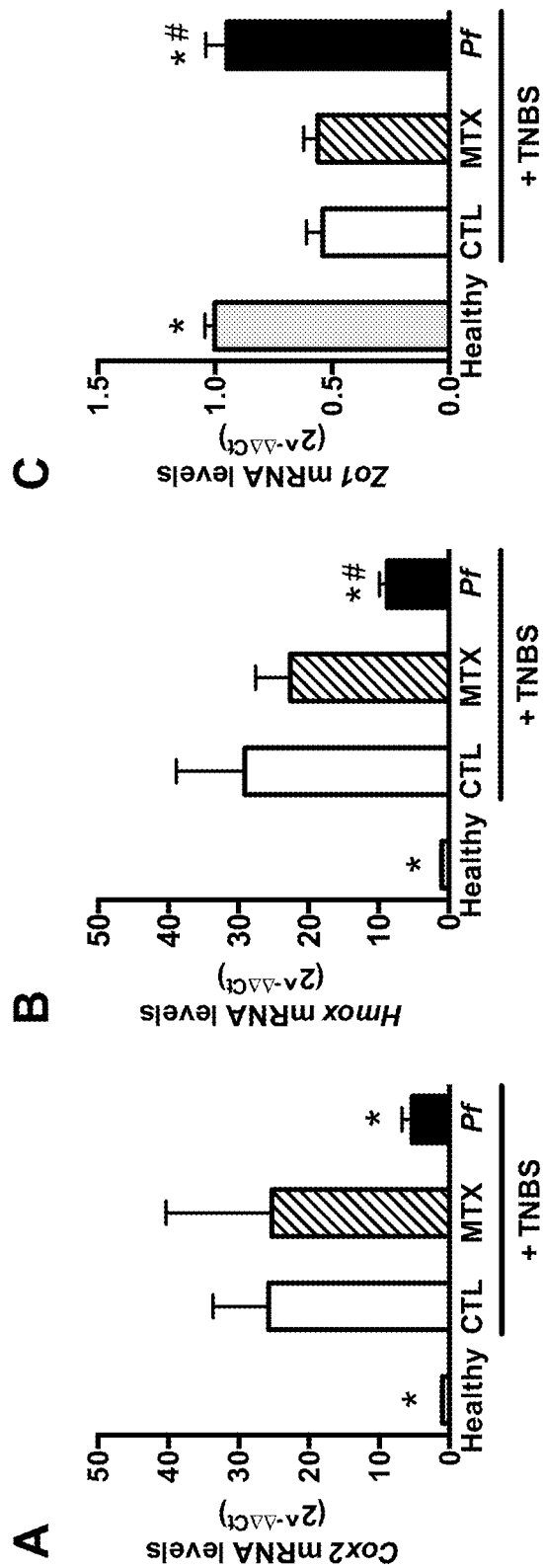
FIG. 9 shows the impact of monoxenic *P. freudenreichii* pressed cheese consumption on colonic oxidative stress and epithelial cell damage in TNBS-induced colitis. (A) Colonic mRNA expression levels of Cox2 in the healthy, CTL, MTX, and Pf groups. (B) Colonic mRNA expression levels of Hmox. (C) Colonic mRNA expression levels of Zo1. The data represent the mean±SEM of 7 to 10 mice per group. *$p<0.05$ versus the CTL group and #$p<0.05$ versus the MTX group.

6.5.4—Monoxenic *P. Freudenreichii* Cheese, But Not Sterile Cheese, Modulates Colonic Oxidative Stress and Epithelial Markers As shown in FIG. 9, TNBS-induced colitis led to colonic oxidative stress as observed by increased levels of Cox2 and Hmox in CTL and MTX groups. Pf cheese intake was associated with decreased mRNA expression levels of these oxidative stress markers. For Cox2 mRNA expression level, there was no significant difference between the CTL and MTX group. By contrast, expression was strongly decreased between MTX and Pf groups (p=0.0608) (FIG. 9A). For Hmox mRNA expression level, Pf cheese intake led to significant decreased level of this marker compared to CTL and MTX groups (FIG. 9B). Finally, Pf cheese intake restored intestinal barrier integrity. Indeed, Zo1 mRNA expression level was quite similar between healthy mice and Pf mice (FIG. 9C). Altogether, Pf cheese intake protected mice against colonic oxidative stress and epithelial cell damages.

6.5.5—A Limited Impact on the Gut Microbiota

Figure 10:
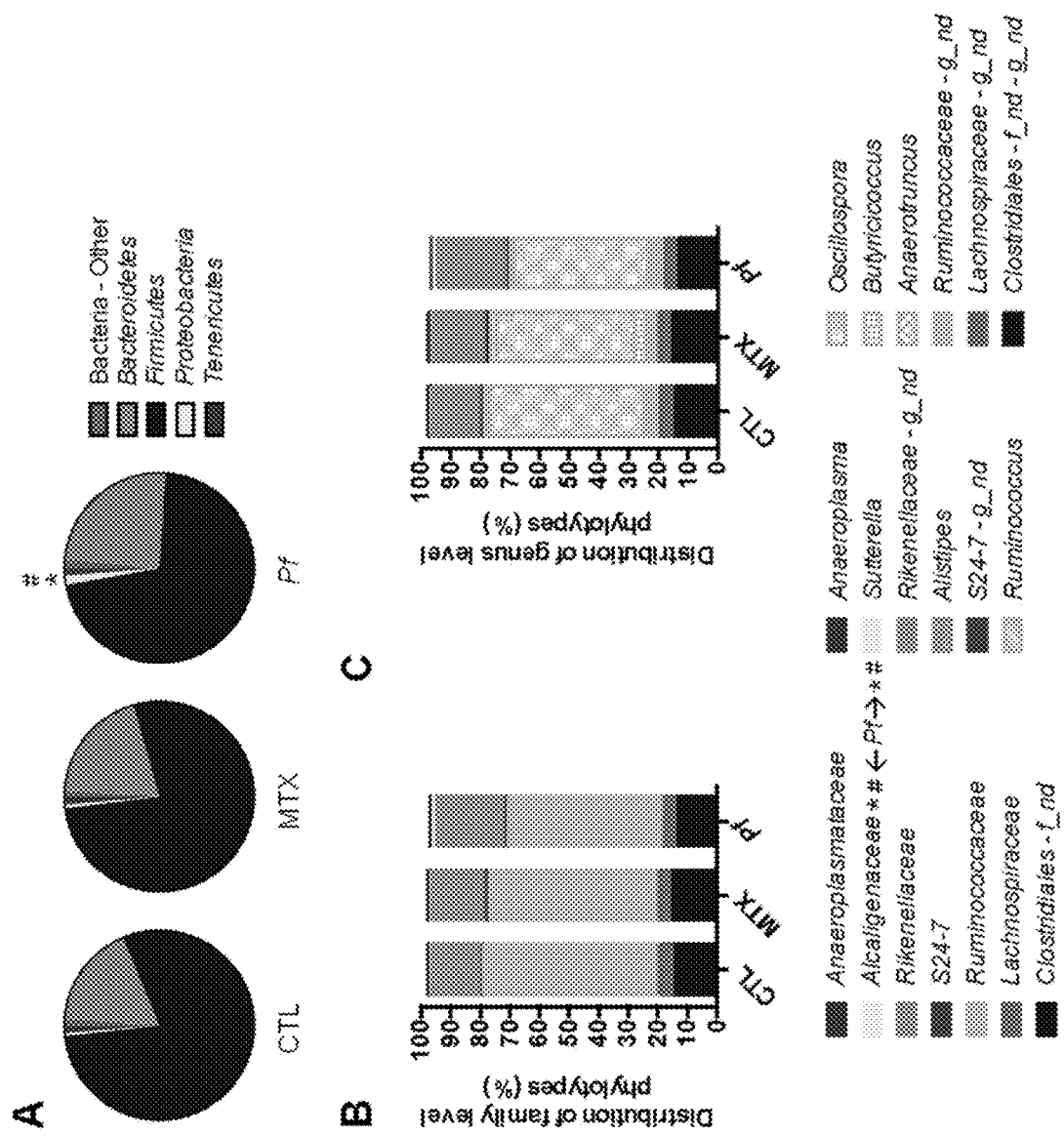
FIG. 10 shows the impact of monoxenic P. freudenreichii pressed cheese consumption on intestinal microbiota. Faeces were collected after 5 days administration of physiological water (CTL group), sterile dairy matrix (MTX) or Pf cheese (Pf) and 454 pyrosequencing of the V3-V4 region of the 16S ribosomal DNA was performed. Distribution of bacteria at (A) phylotype level, (B) family level and (C) genus level. The data represent the mean of 10 mice per group. *$p<0.05$ versus the CTL group and #$p<0.05$ versus the MTX group.

Finally, in order to evaluate the impact of the monoxenic dairy product on the gut microbiota, we analyzed the fecal microbiota after 5 days of dairy product intake. This analysis was carried out via 454 pyrosequencing of the V3-V4 region of the 16S ribosomal DNA. Metagenomic are based on 10 individual samples for each experimental group. The intake of Pf cheese was not associated with major changes in the composition of fecal microbiota at both phylum, family and genus levels compared to CTL and MTX groups. No evidence of major changes in the proportion of Bacteroidetes and Firmicutes were observed (FIG. 10A) while the 5 days-intake of Pf cheese modestly increased Proteobacteria at phylum level. This increase was associated with a slight drop in the proportions of Alcaligenaceae at family level and Sutterella at genus level (FIG. 10A-C). However, it does not seem that such minor changes may explain the further biological effects we observed after the onset of colitis.

The invention claimed is:

1. A method for treating or preventing an inflammatory disease in a patient, comprising administering to a patient in need thereof a therapeutically effective amount of a polypeptide comprising or consisting of an amino acid sequence of a surface layer protein B (SlpB) of *Propinibacterium freudenreichii* or fragment thereof consisting of a processed SlpB protein of *Propinibacterium freudenreichii* devoid of a signal peptide.

2. The method according to claim 1, wherein said inflammatory disease is an inflammatory bowel disease selected from the group consisting of Crohn's disease, ulcerative colitis, ileitis, pouchitis and enteritis.

3. The method according to claim 1, wherein said fragment consists of amino acid 30 to 556 of SEQ ID NO: 1 corresponding to the 527 residues of processed SlpB devoid of the 29 residues of a long signal peptide.

4. The method according to claim 1, wherein the polypeptide is in a pharmaceutical composition comprising a pharmaceutically acceptable carrier.

5. The method of claim 1, wherein the SlpB of *Propinibacterium freudenreichii* is selected from the group consisting of an amino acid sequence of SEQ ID NO: 1 and amino acid sequences having at least 95% of identity with SEQ ID NO: 1and having anti-inflammatory properties of SEQ ID NO: 1.

6. The method of claim 1, wherein the SlpB of *Propinibacterium freudenreichii* is selected the group consisting of an amino acid sequence of SEQ ID NO: 1 and amino acid sequences having at least 99% of identity with SEQ ID NO: 1 and having anti-inflammatory properties of SEQ ID NO: 1.

7. The method of claim 1, wherein the SlpB of *Propinibacterium freudenreichii* is the amino acid sequence of SEQ ID NO: 1.

8. The method of claim 7, wherein said method is for treating for an inflammatory disease in a patient in need thereof.

* * * * *

SEQUENCE LISTING

<160> NUMBER OF SEQ ID NOS: 3

<210> SEQ ID NO 1
<211> LENGTH: 556
<212> TYPE: PRT
<213> ORGANISM: Propionibacterium freudenreichii

<400> SEQUENCE: 1

```
Met Ser Val Arg Lys Ser Leu Thr Gly Met Ala Leu Gly Leu Ala Leu
1               5                   10                  15

Thr Ile Thr Pro Leu Ala Gly Ala Val Pro Ala Ser Ala Asp Thr Ala
            20                  25                  30

Pro Ala Pro Lys Asp Ala Ile Thr Lys Ala Ala Asp Trp Leu Val Asn
        35                  40                  45

Asp Tyr Asn Thr Asn Cys Leu Gly Asp Lys Gln Thr Ser Tyr Ser Cys
    50                  55                  60
```

```
Ser Asn Gly Gly Leu Ala Asp Val Ile Leu Ala Leu Ser Ser Thr Gly
 65                  70                  75                  80

Asp Ala Lys Tyr Ala Asp Glu Ile Ser Thr Met Met Thr Asn Leu Ala
                 85                  90                  95

Pro Gln Val Ala Ser Tyr Thr Lys Asp Asn Ala Gly Ala Thr Ala Lys
            100                 105                 110

Ile Ile Ile Thr Val Ile Ala Ala His Gln Lys Pro Ser Ala Phe Gly
        115                 120                 125

Gly Asn Asp Leu Val Gly Gln Leu Gln Ala Leu Asn Ala Glu Asn Pro
    130                 135                 140

Ala Gly Gly Ala Trp Gly Pro Gln Leu Ser Met Val Ala Leu Thr
145                 150                 155                 160

Arg Ala Gly Glu Thr Val Pro Glu Ala Leu Ile Asp Ala Thr Val Asp
                165                 170                 175

Lys Gln Asn Ser Lys Gly Gly Phe Gly Trp Gly Gly Asp Thr Gly Asp
                180                 185                 190

Gly Asp Asn Thr Ala Ile Gly Met Met Ala Thr Ala Ala Val Ala Lys
            195                 200                 205

Gly Asn Pro Arg Ala Ala Asp Ser Leu Ala Lys Ala Val Ala Trp Ala
    210                 215                 220

Gln Asp Pro Ala Asn Leu Thr Thr Asp Asp Thr Gly Ser Tyr Trp Thr
225                 230                 235                 240

Asn Tyr Ser Pro Thr Asn Thr Ala Gly Met Met Leu Met Ala Ile Gly
                245                 250                 255

Asp Val Asn Asp Pro Lys Ile Asp Val Ser Lys Gln Met Asp Phe Leu
                260                 265                 270

Ile Gly Arg Gln Leu Pro Ser Gly Ala Phe Ser Asn Thr Leu Lys Gly
            275                 280                 285

Thr Asn Asp Asn Ala Met Ala Thr Ile Gln Ala Leu Gln Gly Leu Thr
    290                 295                 300

Met His Gly Tyr Leu Thr Ala Ser Ala Gly Gln Lys Asn Asp Pro Gly
305                 310                 315                 320

Thr Gly Gly Gly Thr Thr Asp Pro Gly Thr Gly Gly Thr Gly Gly
                325                 330                 335

Gly Ser Thr Gly Gly Gly Ser Thr Gly Gly Gly Ser Thr Gly Gly
            340                 345                 350

Gly Gly Ser Thr Gly Gly Gly Ser Thr Gly Gly Gly Val Val
    355                 360                 365

Thr Pro Pro Val Thr Gln Ala Phe Thr Asp Val Ala Pro Ser Asn Met
370                 375                 380

Tyr Phe Thr Glu Ile Gln Trp Ala Ala Ala Asn Asn Val Thr Thr Gly
385                 390                 395                 400

Trp Lys Asn Ala Asp Gly Thr Ala Ser Phe Arg Pro Leu Asp Thr Thr
                405                 410                 415

His Arg Asp Ala Met Ala Ala Phe Leu Tyr Arg Leu Ser Gly Ser Pro
                420                 425                 430

Ser Tyr Thr Ala Pro Ala Thr Ser Pro Phe Thr Asp Val Asn Pro Ser
            435                 440                 445

Asn Gln Phe Tyr Lys Glu Ile Cys Trp Leu Ala Ser Gln Asn Ile Thr
    450                 455                 460

Thr Gly Trp Pro Asp Gly Ser Phe Arg Pro Leu Asp Asn Val Asn Arg
465                 470                 475                 480
```

```
Asp Ala Met Ala Ala Phe Leu Tyr Arg Tyr Ser Gln Val Ser Gly Phe
                485                 490                 495

Gln Ala Pro Ala Ala Ser Pro Phe Ala Asp Val Thr Pro Gly Ser Gln
            500                 505                 510

Phe Tyr Thr Glu Met Ser Trp Leu Ser Ala Asn Gly Ile Ser Thr Gly
        515                 520                 525

Trp Pro Asp Gln Thr Phe Arg Pro Val Thr Pro Ile Ala Arg Asp Ala
530                 535                 540

Met Ile Thr Phe Ile Tyr Arg Met Lys His Ala Ser
545                 550                 555

<210> SEQ ID NO 2
<211> LENGTH: 1671
<212> TYPE: DNA
<213> ORGANISM: Propionibacterium freudenreichii

<400> SEQUENCE: 2
atgtccgtca ggaagagcct gaccgggatg gcgctggggc ttgccctcac catcaccccg      60
ctcgccggcg cggttccggc gtcagccgac accgcaccgg cccccaagga tgccatcacc     120
aaggcagccg attggctggt gaatgattac aacaccaatt gtcttggcga caagcagaca     180
agttatagct gctcgaacgg cggcctggcc gatgtcatcc tggccctgtc atccaccggt     240
gacgcgaaat atgccgacga gatctccacc atgatgacga atttggcacc gcaggtggcc     300
agctacacga aggacaatgc gggcgctacc gccaagatca tcatcactgt cattgccgcc     360
catcagaaac cgagtgcctt tggggggaat gacctggtgg ccagttgca ggcactgaac      420
gcggagaacc ccgccggtgg cggggcatgg ggaccgcagt tgtcgatggt ggctctcacc     480
cgcgccgggg agaccgtgcc cgaggcactg atcgatgcga cagtggacaa gcaaaacagc     540
aagggcggct tcggctgggg cggcgacacg ggcgatggcg acaacaccgc gatcggcatg     600
atggccaccg cggccgtcgc caagggcaac cccagggcag ccgactcgct cgccaaggcg     660
gtcgcctggg cccaggaccc ggccaacctc accaccgatg acaccggaag ctactggacc     720
aactactcgc ccaccaacac tgcgggcatg atgctcatgg ccatcggcga cgtgaacgac     780
cccaagatcg acgtcagcaa gcagatggac ttcctgatcg gtcgccagct gcccagtggc     840
gccttctcga cacactcaa gggcaccaac gacaatgcga tggccaccat ccaggccctc      900
cagggcctca cgatgcacgg ctacctgacc gcttcggccg ccagaagaa tgacccgggc      960
accggcggtg gcacgacgga tccgggcacc ggcggcggca cgggtggcgg atcgaccggc    1020
ggcggctcaa ctggcggtgg cggtagcacc ggcggcggag atcgaccgg cggtggcggt     1080
agcaccggtg gcggcggcgt tgtcacgccc ccggtcaccc aggccttcac cgatgttgcc    1140
ccgagcaaca tgtacttcac cgagatccag tgggcggccg ccaacaatgt gaccaccggc    1200
tggaagaacg ccgatggcac ggcgtcgttc cgtccgctcg acaccacgca ccgcgacgca    1260
atggcggcgt tcctctaccg cctgagtgga tcgccgagct acaccgcccc ggccacctcg    1320
ccgttcaccg acgtcaaccc gtcgaaccag ttctacaagg agatctgctg gctcgcctcg    1380
cagaacatca ccaccggctg gcccgacggc agcttccggc cactggacaa tgtgaaccgc    1440
gacgcgatgg cggccttcct gtaccgctac tcgcaggtct cgggcttcca ggccccggct    1500
gcttcgccgt tcgctgacgt gacgcccggc agccagttct acaccgagat gtcgtggctg    1560
tcagccaacg gcatctccac cggttggccc gaccagacgt tccgtccggt gacgccgatc    1620
gcccgcgacg cgatgatcac cttcatctat cgcatgaagc acgccagctg a             1671
```

```
<210> SEQ ID NO 3
<211> LENGTH: 574
<212> TYPE: DNA
<213> ORGANISM: Artificial Sequence
<220> FEATURE:
<223> OTHER INFORMATION: internal sequence of slpB

<400> SEQUENCE: 3
agcttaacta ctcgcccacc aacactgcgg gcatgatgct catggccatc ggcgacgtga     60
acgaccccaa gatcgacgtc agcaagcaga tggacttcct gatcggtcgc cagctgccca    120
gtggcgcctt ctcgaacaca ctcaagggca ccaacgacaa tgcgatggcc accatccagg    180
ccctccaggg cctcacgatg cacggctacc tgaccgcttc ggccggccag aagaatgacc    240
cgggcaccgg cggtggcacg acggatccgg gcaccggcgg cggcacgggt ggcggatcga    300
ccggcggcgg ctcaactggc ggtggcggta gcaccggcgg cggaggatcg accggcggtg    360
gcggtagcac cggtggcggc ggcgttgtca cgcccccggt cacccaggcc ttcaccgatg    420
ttgccccgag caacatgtac ttcaccgaga tccagtgggc ggccgccaac aatgtgacca    480
ccggctggaa gaacgccgat ggcacggcgt cgttccgtcc gctcgacacc acgcaccgcg    540
acgcaatggc ggcgttcctc taccgcctga gtga                                574
```